United States Patent
Satou et al.

(10) Patent No.: US 9,514,253 B2
(45) Date of Patent: Dec. 6, 2016

(54) MOLECULAR DESIGN APPARATUS AND METHOD

(71) Applicant: Fujitsu Limited, Kawasaki-shi (JP)

(72) Inventors: Hiroyuki Satou, Kawasaki (JP); Azuma Matsuura, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 961 days.

(21) Appl. No.: 13/692,546

(22) Filed: Dec. 3, 2012

(65) Prior Publication Data

US 2013/0197879 A1    Aug. 1, 2013

(30) Foreign Application Priority Data

Feb. 1, 2012   (JP) .................................. 2012-020255

(51) Int. Cl.
G06F 7/60       (2006.01)
G06F 17/10      (2006.01)
G06F 17/50      (2006.01)
G09B 23/26      (2006.01)
G06F 19/00      (2011.01)

(52) U.S. Cl.
CPC ........... *G06F 17/5009* (2013.01); *G09B 23/26* (2013.01); *G06F 19/701* (2013.01)

(58) Field of Classification Search
CPC .. G06F 17/5009; G06F 17/50; G06F 19/701; G09B 23/26
USPC ........................................ 703/2, 12; 345/419
See application file for complete search history.

(56) References Cited

U.S. PATENT DOCUMENTS

| | | | |
|---|---|---|---|
| 5,572,439 A | 11/1996 | Nishida et al. | |
| 8,126,656 B2 | 2/2012 | Sato et al. | |
| 2005/0119835 A1* | 6/2005 | Kita | G06F 19/16 702/19 |
| 2008/0059549 A1* | 3/2008 | Aoki | G06F 19/701 708/401 |

FOREIGN PATENT DOCUMENTS

| | | | |
|---|---|---|---|
| JP | 06-168304 | | 6/1994 |
| JP | 08-016546 | | 1/1996 |
| JP | 8016546 | * | 1/1996 |
| WO | WO-2008/096424 A1 | | 8/2008 |

OTHER PUBLICATIONS

Fornilli, Arianna et al. "Determination of Extremely Localized Molecular Orbitals and their Application to Quantum Mechanics/Molecular Mechanics Methods and to the Study of Intramolecular Hydrogen Bonding", 2003, Journal of Molecular Structure (Theochem) 632, Elsevier B.V.*

(Continued)

Primary Examiner — Cedric D Johnson
(74) Attorney, Agent, or Firm — Fujitsu Patent Center

(57) ABSTRACT

A molecular design apparatus is disclosed. Expansion coefficients applied to basis functions are calculated by expanding molecular orbital functions used to draw molecular orbitals based on the molecular structure design data. First molecular orbital data in which the expansion coefficients are corresponded to the basis functions is stored to the storage part. A coefficient threshold is determined for the expansion coefficients of the basis functions by using a drawing threshold which indicates a constant function value, to draw the molecular orbital functions as an isosurface of the constant function value on a screen of a display device. Second molecular orbital data pertinent to the expansion coefficients is stored based on the coefficient threshold to the storage part.

7 Claims, 14 Drawing Sheets

MAXIMUM NUMBER OF ATOMS IN SPHERE: $N_{max}^{Atom}$

(56) References Cited

OTHER PUBLICATIONS

Autschbach, Jochen "Analyzing NMR Shielding Tensors Calculated with Two-Component Relativistic Methods Using Spin-Free Localized Molecular Orbitals", Apr. 25, 2008, The Journal of Chemical Physics, 128, Americal Institute of Physics.*

Ylvisaker, Erik Ryan, "DFT and DMFT: Implementations and Applications to the Study of Correlated Materials", 2008, University of California Davis.*

Halls, Mathew D. et al., "Molecular Orbital Study of the First Excited State of the OLED Material Tris (8-Hydroxyquinoline) Aluminum (III)", Jun. 30, 2001, Chem. Mater. 13, American Chemical Society.*

Rittenhouse, S.T. et al., "The Hyperspherical Four-Fermion Problem", Aug. 12, 2011, Journal of Physics B: Atomic, Molecular and Optical Physics 44, IOP Publishing, Ltd.*

Tomasi, Jacopo et al., "Molecular Interactions in Solution: An Overview of Methods Based on Continuous Distributions of the Solvent", 1994, Chem. Review, 94, Americal Chemical Society.*

Extended European Search Report dated May 16, 2013 for corresponding European Application No. 12194942.4.

* cited by examiner

MAXIMUM NUMBER OF ATOMS IN SPHERE: $N_{max}^{Atom}$

THREE-DIMENSIONAL MOLECULAR STRUCTURE 8b
1BFP

HOMO 8a

MOLECULAR DESIGN APPARATUS AND METHOD

CROSS-REFERENCE TO RELATED APPLICATIONS

This patent application is based upon and claims the benefit of priority of the prior Japanese Patent Application No. 2012-020255 filed on Feb. 1, 2012, the entire contents of which are incorporated herein by reference.

FIELD

The embodiment discussed herein is related to a molecular design apparatus and method for drawing molecular orbitals on a screen of a display device based on molecular structure design data.

BACKGROUND

In research and development of a high technology related to drug design or the like, needs of a molecular orbital calculation using a computer have been increased. The molecular orbital function is useful for research of photo-responsiveness and reactivity of a molecule to be a development target. Especially, molecular orbitals such as a HOMO (Highest Occupied Molecular Orbital) and a LUMO (Lowest Unoccupied Molecular Orbital) are frequently drawn by a three-dimensional drawing using the computer. In order to draw the molecular orbitals, a molecular orbital drawing program and a molecular orbital drawing apparatus are used. A GUI (Graphical User Interface) for an easy user operation is realized.

However, in the above-described drawing of the molecular orbitals, especially in a case of handling a large scale molecule, a calculation using a large amount of data is performed. In many molecular orbital calculation programs, expansion coefficients of the molecular orbitals acquired from a molecular orbital calculation result are output to a file. By a molecular orbital drawing program, a drawing process is executed. In the drawing process, expansion coefficient data and basis function data are read out from the file and values of molecular orbital functions are calculated. Alternatively, in addition to the file to which the expansion coefficients are output, a result file may be output as a result from actually calculating function values of three-dimensional lattice points. The molecular orbital drawing program may read the result file, and then, the drawing process may be performed.

In a case in which a data amount related to the drawing process is increased, a drawing time may be delayed. In order to improve drawing speed, values of basis functions of the three-dimensional lattice points may be calculated beforehand. Moreover, lattice points themselves may be reduced.

Patent Documents

Japanese Laid-open Patent Publication No. H06-168304
Japanese Laid-open Patent Publication No. H08-16546

SUMMARY

According to one aspect of the embodiment, there is provided a molecular design apparatus, including a storage part configured to store molecular structure design data; a molecular orbital function expansion part configured to calculate expansion coefficients applied to basis functions by expanding a molecular orbital function used to draw molecular orbitals based on the molecular structure design data, and stores first molecular orbital data in which the expansion coefficients are corresponded to the basis functions to the storage part; and a molecular orbital data reduction part configured to determine a coefficient threshold for the expansion coefficients of the basis functions acquired by the molecular orbital function expansion part by using a drawing threshold which indicates a constant function value, to draw the molecular orbital functions as an isosurface of the constant function value on a screen of a display device, and to store second molecular orbital data pertinent to the expansion coefficients based on the coefficient threshold to the storage part.

According to other aspects of the embodiment, there may be provided a molecular design method conducted by a computer, and a non-transitory computer-readable recording medium storing a program for causing the computer to operate as the above-described molecular design apparatus.

The object and advantages of the invention will be realized and attained by means of the elements and combinations particularly pointed out in the appended claims. It is to be understood that both the foregoing general description and the following detailed description are exemplary and explanatory and are not restrictive of the invention as claimed.

DESCRIPTION OF EMBODIMENTS

Figure 1:
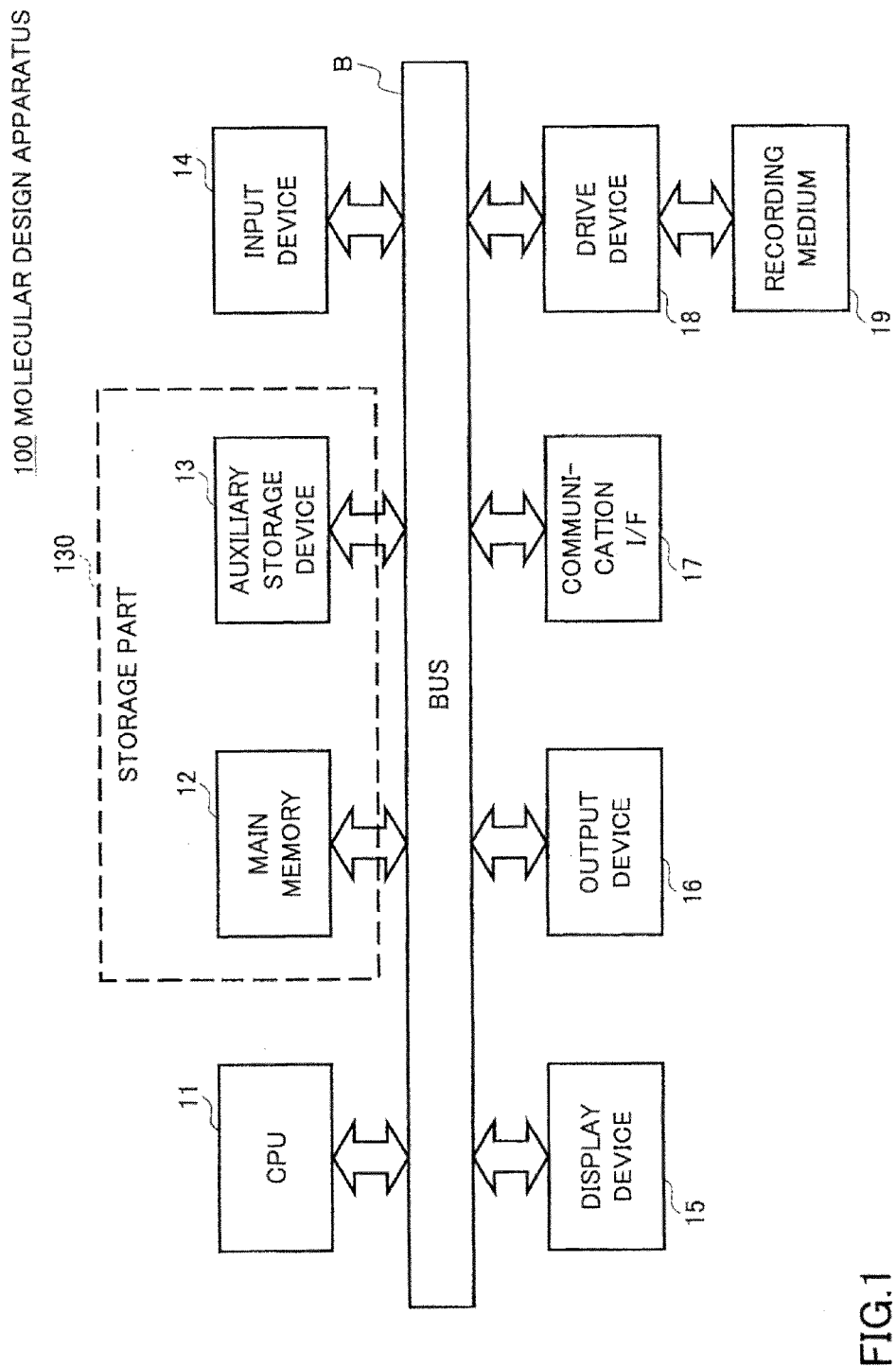
FIG. 1 is a diagram illustrating a hardware configuration of a molecular design apparatus.

In the following, an embodiment of the present invention will be described with reference to the accompanying drawings. A molecular design apparatus 100 according to the embodiment includes a hardware configuration as illustrated in FIG. 1. FIG. 1 is a diagram illustrating the hardware configuration of the molecular design apparatus 100. In FIG.

1, the molecular design apparatus 100 may be a terminal controlled by a computer, and may include a CPU (Central Processing Unit) 11, a main memory 12, an auxiliary storage device 13, an input device 14, a display device 15, an output device 16, a communication interface (I/F) 17, and a drive device 18, which are mutually connected via a bus B.

The CPU 11 controls the molecular design apparatus 100 in accordance with programs stored in the main memory 12. The main memory 12 may include a Random Access Memory (RAM), a ROM (Read-Only Memory), or the like. The main memory 12 stores programs executed by the CPU 11, data used in processes conducted by the CPU 11, data acquired in the processes conducted by the CPU 11, and the like. Also, a part of an area of the main memory 12 may be used as a working area for the processes conducted by the CPU 11.

The auxiliary storage device 13 may include a hard disk drive, and may store data such as the programs to perform various processes. A part of a program stored in the auxiliary storage device 13 is loaded to the main memory 12, and is executed by the CPU 11. Accordingly, various processes are realized. A storage part 130 may include the main memory 12 and/or the auxiliary storage device 13.

The input device 14 may include one or more operation parts such as a pointing device such as a mouse, a keyboard or the like. The input device 14 may be used for a user to input various information items for the processes in the molecular design apparatus 100. The display device 15 is used to display various information items under a control of the CPU 11. The output device 16 may include a printer or the like. The output device 16 is used for the user to output various information items in response to an instruction of the user. The communication I/F 17 is used to connect to the Internet, a Local Area Network (LAN), or the like. The communication I/F 17 corresponds to a device for controlling a communication with an external device.

The program, which may realize the process performed by the molecular design apparatus 100, may be provided by a recording medium 19 such as a CD-ROM (Compact Disc Read-Only Memory) or the like. That is, when the recording medium 19 storing the program is set to the drive device 18, the program is read out by the drive device 18 from the recording medium 19, and is installed to the auxiliary storage device 13 through the bus B. Accordingly, when the CPU 11 is instructed to execute the program, the CPU 11 starts the process in accordance with the program installed in the auxiliary storage device 13. The recording medium 19 for storing the program is not limited to the CD-ROM. Any computer-readable recording medium may be used as the recording medium 19. In addition to the CD-ROM, a portable recording medium such as a Digital Versatile Disk (DVD), a Universal Serial Bus (USB) memory, a semiconductor memory such as a flash memory, or the like may be used as the computer-readable recording medium 19.

Also, the program for realizing the process performed by the molecular design apparatus 100 may be provided from the external device through the communication I/F 17. Alternatively, the program may be provided to the external device. Each of processes, which will be described later, may be realized at the external device. The communication through the communication I/F 17 is not limited to a wireless or wired communication.

Figure 2:
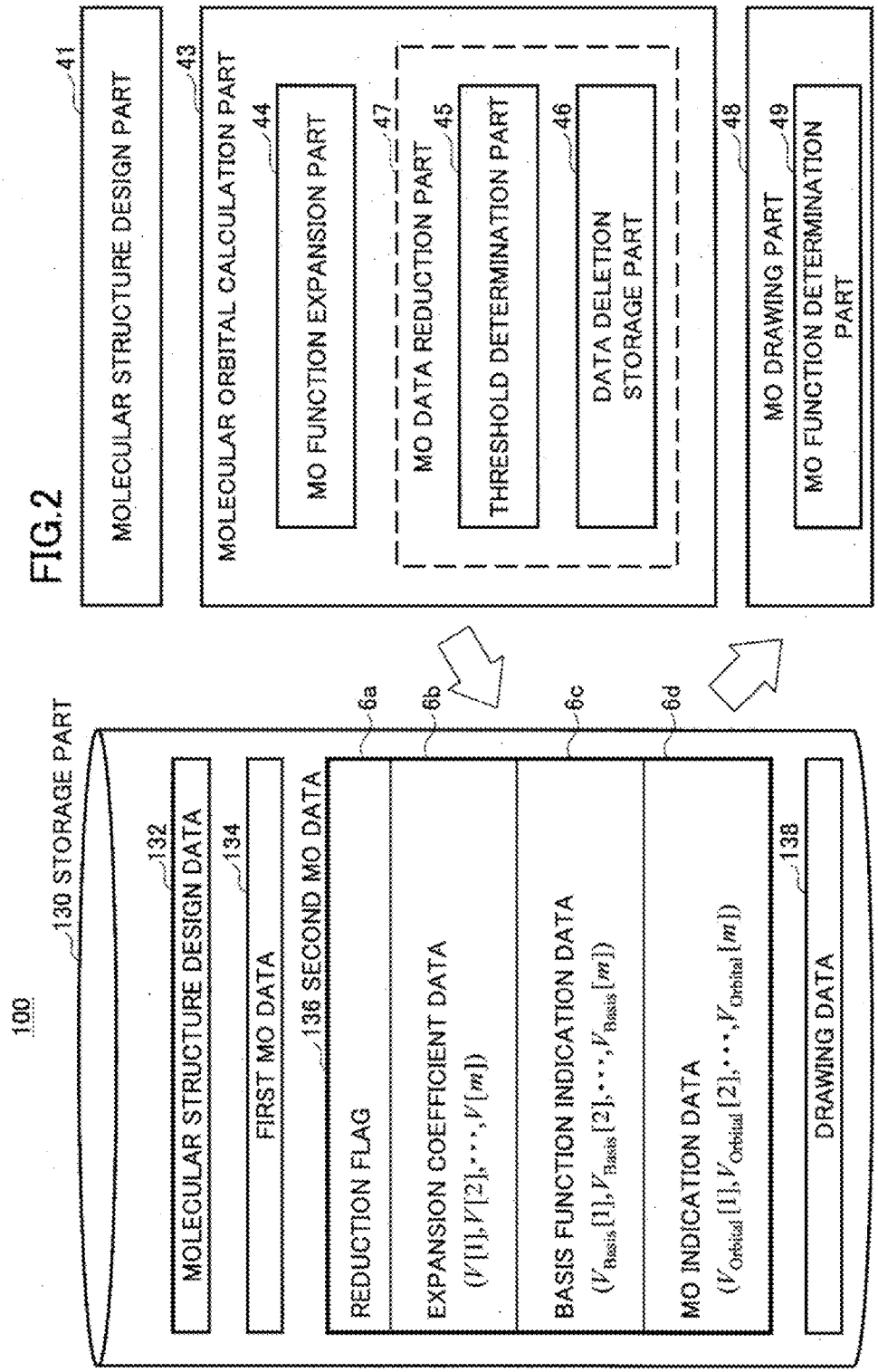
FIG. 2 is a diagram illustrating a functional configuration example of the molecular design apparatus.

FIG. 2 is a diagram illustrating a functional configuration example of the molecular design apparatus 100. In FIG. 2, portions according to the embodiment will be illustrated, and other portions are omitted. In FIG. 2, the molecular design apparatus 100 includes a molecular structure design part 41, a molecular orbital calculation part 43, and a molecular orbital (MO) function expansion part 44, and an MO drawing part 48. The molecular structure design part 41, the MO function expansion part 44, and the MO drawing part 48 may be realized by processes which are performed by the CPU 11 executing respective programs.

The molecular structure design part 41 conducts the molecular structure design based on data pertaining to the molecular structure. The data are input from the input device 14 by the user. A main window for the user to work is displayed by the molecular structure design part 41 on a screen of the display device 15. The user operates an atom item, a bond axis item, and the like to be displayed in the main window, by using the pointing device, the keyboard, or the like, so as to build a three-dimensional structure of a molecule in the main window. Molecular structure design data 132, which is created by operations of the user, are stored in the storage part 130.

The molecular orbital calculation part 43 calculates a molecular orbital based on the molecular structure design data 132. In the embodiment, the molecular orbital calculation part 43 reduces as much as possible a data amount of a calculation result of the molecular orbital without losing drawing data of the molecular orbital.

The molecular orbital calculation part 43 calculates the molecular orbital based on the molecular structure design data 132 by a molecular orbital function represented by a linear combination of multiple basis functions which are prepared beforehand. The molecular orbital calculation part 43 further includes the MO function expansion part 44, a threshold determination part 45, and a data deletion storage part 46. The threshold determination part 45 and the data deletion storage part 46 correspond to a MO data reduction part 47 for reducing the data amount of the calculation result of the molecular orbital.

The MO function expansion part 44 calculates coefficients (hereinafter, called "expansion coefficients") concerning the multiple basis functions to expand the molecular orbital function into the multiple basis functions. In the embodiment, the molecular orbital calculation is performed to acquire the expansion coefficients respective to the multiple molecular orbital functions. In the following, the "molecular orbital" and the "molecular orbital function" are synonymous in a molecular orbital calculation process. The molecular orbital function represents a state of an electron in a molecule. An orbital function value in coordinates is raised to the power of two. In detail, by using an expression (1), the expansion coefficients of the molecular orbital function are calculated.

$$\phi_i(r) = \sum_{p=1}^{N} C_{pi}\chi_p(r) \tag{1}$$

In the above expression (1), $\phi_i$ indicates an $i^{th}$ molecular orbital function, r indicates coordinates used to acquire a function value, and $\chi_p$ indicates a $p^{th}$ basis function. N indicates a total number of the basis functions, and $C_{pi}$ indicates an expansion coefficient applied to the $p^{th}$ basis function in a case in which an $i^{th}$ molecular orbital function is expanded into the multiple basis functions. First MO data 134 are stored in the storage part 130. In the first MO data 134, the expansion coefficients $C_{pi}$ correspond to the $p^{th}$ basis function for each $i^{th}$ molecular orbital function.

The threshold determination part 45 determines thresholds of the above-described coefficients used to create second MO data 136 for drawing the molecular orbital. By using the second MO data 136, it is possible for the MO drawing part 48 to draw the molecular orbital at high speed. A coefficient threshold $C_{cutoff}$ is determined by an expression (3) acquired from an expression (2) based on the expression (1).

$$\phi_{cutoff} = (\alpha \times N_{max}^{Atom}) \times C_{cutoff} \times \chi_{cutoff} \quad (2)$$

$$C_{cutoff} = \frac{\phi_{cutoff}}{\alpha N_{max}^{Atom} \chi_{cutoff}} \quad (3)$$

In the above expressions (2) and (3), in a case in which the molecular orbital is drawn, $\phi_{cutoff}$ represents a threshold (corresponding to a drawing threshold) of the molecular orbital to set to an isosurface. Also, $\alpha$ represents a value acquired by multiplying the number of the basis functions belonging to each of atoms with a ratio of the number of electrons with respect to a total number of basis, a basis ratio respective to the value, or the like. $N^{Atom}_{max}$ represents a maximum value of atoms in a range where the basis functions are overlapped. The coefficient threshold $C_{cutoff}$ represents a threshold of the expansion coefficient of the molecular orbital function. $\chi_{cutoff}$ represents a threshold of the basis function to ignore relationships with other basis functions, regarding a radial distribution function of the basis function.

The data deletion storage part 46 reduces the data amount of the first MO data 134, and also stores the second MO data 136 for the MO drawing part 48 to acquire an approximate molecular orbital function.

The data deletion storage part 46 specifies, by referring to the first MO data 134, the expansion coefficients $C_{pi}$ being greater than or equal to coefficient threshold $C_{cutoff}$ calculated by a threshold determination part 45, the basis function $\chi_p$ corresponding to the expansion coefficients $C_{pi}$, and the number of elements to acquire the approximate molecular orbital function for the $i^{th}$ molecular orbital function acquired by the MO function expansion part 44. The data deletion storage part 46 stores the expansion coefficients $C_{pi}$, the basis function $\chi_p$, and the number of elements to the second MO data 136 in the storage part 130, and sets "True" to a reduction flag 6a of the second MO data 136 to validate the second MO data 136. Initially, "False" is set to the reduction flag 6a to invalidate the second MO data 136.

The expansion coefficients $C_{pi}$ being greater than or equal to the coefficient threshold $C_{cutoff}$ is stored in expansion coefficient data 6b. Preferably, the expansion coefficients $C_{pi}$ may be stored in one dimensional array V. Basis function indication data 6c stores an entity of the basis function $\chi_p$ corresponding to the expansion coefficients $C_{pi}$ stored in the expansion coefficient data 6b, or a pointer to the basis function $\chi_p$ existing in the first MO data 134. In this case, one dimensional array $V_{Basis}$ may be used for the basis function $\chi_p$. Also, the number of the basis functions $\chi_p$, which is applied after the reduction of the data amount, corresponds to an element number of the array $V_{Basis}$. One dimensional array $V_{Orbital}$ represents elements of the array V for the expansion coefficients $C_{pi}$ for each of the molecular orbital functions, and is stored in MO indication data 6d.

The MO drawing part 48 draws the molecular orbital on the molecular structure in the window of the display device 15 by using the molecular orbital function calculated by the molecular orbital calculation part 43. If the reduction flag 6a of the second MO data 136 indicates "True" (the second MO data 136 is validated), the molecular orbital drawing part 48 draws the molecular orbital on the molecular structure by using the approximate molecular orbital function by referring to the second MO data 136. On the other hand, if the reduction flag 6a indicates "False" (the second MO data 136 is invalidated), the molecular orbital drawing part 48 draws the molecular orbital on the molecular structure by using the first MO data 134.

The molecular orbital drawing part 48 includes a MO function determination part 49. If the reduction flag 6a indicates "True", the MO function determination part 49 calculates approximate molecular orbital function by referring to the second MO data 136. The molecular orbital drawing part 48 acquires a molecular orbital function value by using the approximate molecular orbital function calculated by the MO function determination part 49, and draws the molecular orbital on the molecular structure based on the molecular structure design data 132. Drawing data 138 for drawing the molecular orbital on the molecular structure are stored in the storage part 130.

Next, a threshold determination process will be described. The threshold determination process is performed by the threshold determination part 45 to reduce the data amount of the expansion coefficients of the molecular orbitals.

The threshold determination part 45 acquires each of the following values to calculate the coefficient threshold $C_{cutoff}$ indicating a threshold value of the expansion coefficients of the molecular orbital functions, in which the coefficient threshold $C_{cutoff}$ is expressed by the above expression (3).
(A1) a drawing threshold $\phi_{cutoff}$ for the molecular orbital functions to draw the molecular orbitals,
(A2) a base threshold $\chi_{cutoff}$ in which influence to other basis functions becomes sufficiently small in a space distribution of the basis function,
(A3) a threshold $r^{\chi}_{max}$ of a distance where the basis function and other basis functions are sufficiently overlapped,
(A4) a maximum value $N^{Atom}_{max}$ of the number of atoms included in a sphere having a radius $2r^{\chi}_{max}$ from a center of each of the atoms,
(A5) a value $\alpha$ acquired by multiplying the number of bases for each of the atoms with a ratio of the number of electrons with respect to a total number of bases, and the like.

Figure 3:
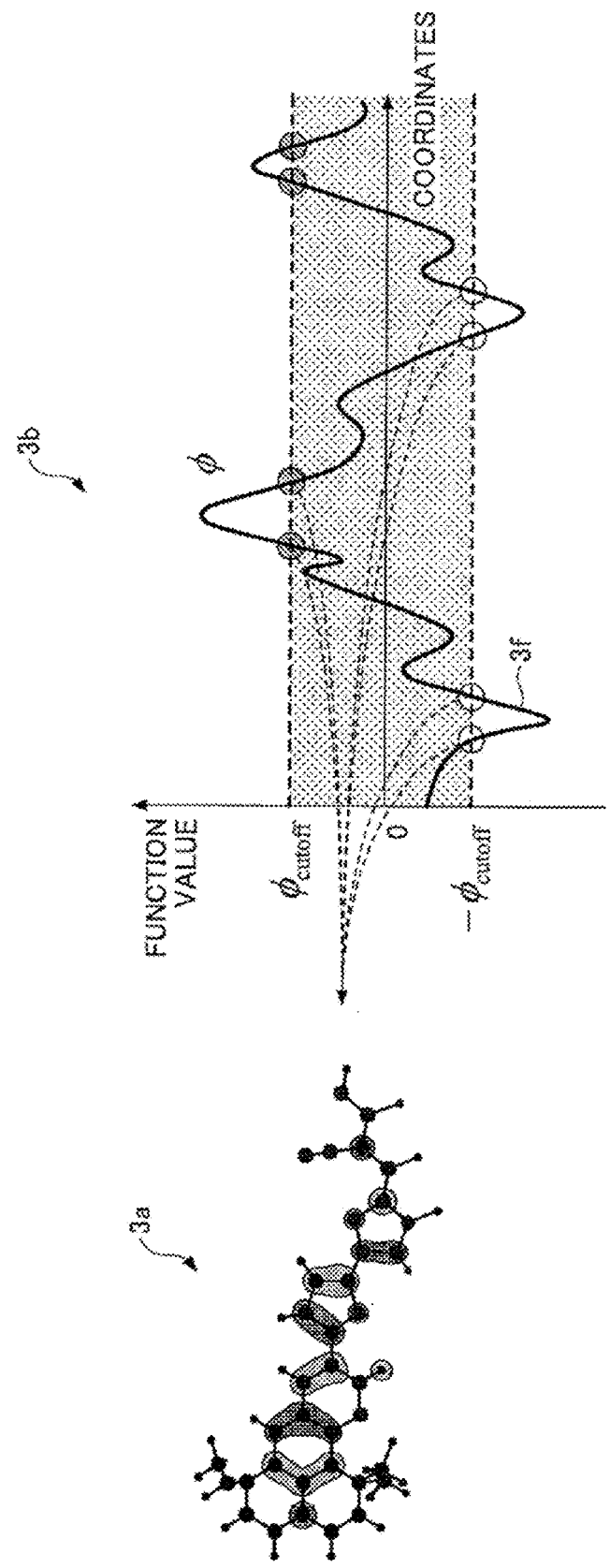
FIG. 3 is a diagram for explaining a drawing threshold $\phi_{cutoff}$ for molecular orbital functions.

The above item (A1) will be described with reference to FIG. 3. FIG. 3 is a diagram for explaining the drawing threshold $\phi_{cutoff}$ for the molecular orbital functions. In a graph 3b illustrated in FIG. 3, a vertical axis indicates a function value, and a horizontal axis indicates coordinates. Drawing using the molecular orbital functions may be performed as drawing isosurface determined by an absolute value of a certain function value. By setting the drawing threshold $\phi_{cutoff}$ of a function 3f, function values between $+\phi_{cutoff}$ and $-\phi_{cutoff}$ are not used. The MO drawing part 48 displays a molecular structure 3a at the display device 15. In the molecular structure 3a, the molecular orbitals are drawn by using the function values which are greater than or equal to $+\phi_{cutoff}$ or less than or equal to $-\phi_{cutoff}$. The drawing threshold $\phi_{cutoff}$ may be a value set by a user.

Figure 4:
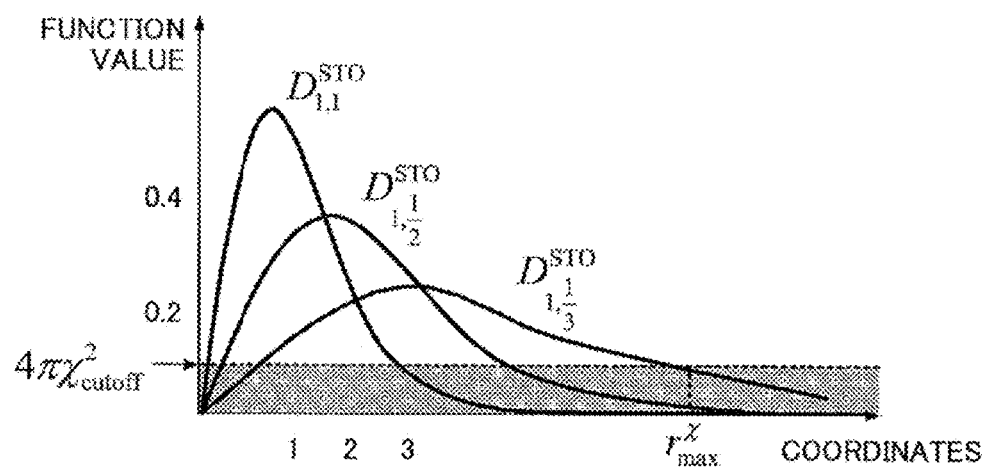
FIG. 4 is a diagram for explaining a basis threshold $\chi_{cutoff}$.

The above items (A2) and (A3) will be described with reference to FIG. 4. FIG. 4 is a diagram for explaining the basis threshold $\chi_{cutoff}$. In FIG. 4, the basis threshold $\chi_{cutoff}$ indicates a threshold in which influence from the basis functions to other basis functions becomes sufficiently smaller. The basis functions are used to expand to the molecular orbital functions. Basis function values being less than or equal to the basis threshold $\chi_{cutoff}$ are deleted.

In a case of considering the influence to the other basis functions, a distribution function D (an expression (6)) may be used. The distribution function D may be regarded as a distribution function of a radial function R (an expression (5)) forming a basis function χ (an expression (4)).

$$\chi_{nlm}^{STO} = R_n^{STO}(r) Y_{lm}(\theta, \varphi) \quad (4)$$

$$R_n^{STO}(r) = \frac{(2\varsigma)^{3/2}}{\sqrt{\Gamma(2n+1)}} (2\varsigma r)^{n-1} \exp(-\varsigma r) \quad (5)$$

$$D_{n,\varsigma}^{STO}(r) = 4\pi [R_n^{STO}(r)]^2 \quad (6)$$

In the expressions (4) to (6), $\chi^{STO}_{nlm}$ indicates a basis function using a Slater Type Orbital (STO), n indicates a principal quantum number, l indicates an azimuthal quantum number, and m indicates a magnetic quantum number. $R^{STO}_n(r)$ indicates the radial function of the Slater Type Orbital in radial coordinates r, and n indicates the principal quantum number. $Y_{lm}(\theta,\phi)$ indicates spherical harmonics of the Slater Type Orbital in angular coordinates θ and φ, l indicates the azimuthal quantum number, and m indicates a magnetic quantum number.

ζ indicates an orbital exponent (a coefficient of an exponent of the radial function). $D^{STO}_{n,\varsigma}$ indicates a radial distribution function of the Slater Type Orbital, and n indicates the principal quantum number. Also, $r^\chi_{max}$ indicates the radial coordinates determined by the threshold of the basis function.

Figure 5:
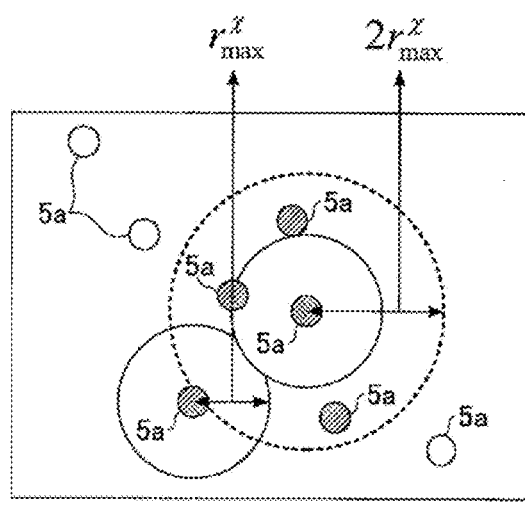
FIG. 5 is a diagram for explaining a maximum number $N^{Atom}_{max}$.

The above item (A4) will be described with reference to FIG. 5. FIG. 5 is a diagram for explaining the maximum number $N^{Atom}_{max}$. The maximum number $N^{Atom}_{max}$ indicates a maximum value of the total number of atoms 5a in a case of considering the influence of the basis function belonging to an atom 5a to other basis functions belonging to other atoms 5a for each atom. Coordinates are set as $r^\chi_{max}$ when the coordinates indicate a function value of the distribution function D corresponding to the basis threshold (FIG. 4). In this case, if centers of other atoms 5a are included in a sphere of a radius $2r^\chi_{max}$ from each of the atoms 5a, it is considered that the basis functions may influence each other (FIG. 5).

In FIG. 5, $N^{Atom}_{max}$ indicates the maximum value of the number of the atoms 5a included in the sphere of the radius $2r^\chi_{max}$ from the center of each of the atoms 5a.

The above item (A5) will be described. α indicates a value which results from multiplying the number of the basis functions belonging to each of the atoms 5a with a ratio of an electron number with respect to the total number of the basis functions, or an other value respective to the calculated value. When a is calculated, a HOMO (Highest Occupied Molecular Orbital) in a region which tends to give an electron or a LUMO (Lowest Unoccupied Molecular Orbital) in a region which tends to receive the electron may be considered. $\alpha N^{Atom}_{max}$ is regarded as the number of the basis functions which are actually overlapped with respect to the total number N of the basis functions in the expression (1) for calculating the molecular orbital functions. Accordingly, it is possible to determine the drawing threshold $\phi_{cutoff}$ based on a relational expression (the above expression (2)), and to determine a pertinent coefficient threshold $C_{cutoff}$ by the above expression (3).

Figure 6:
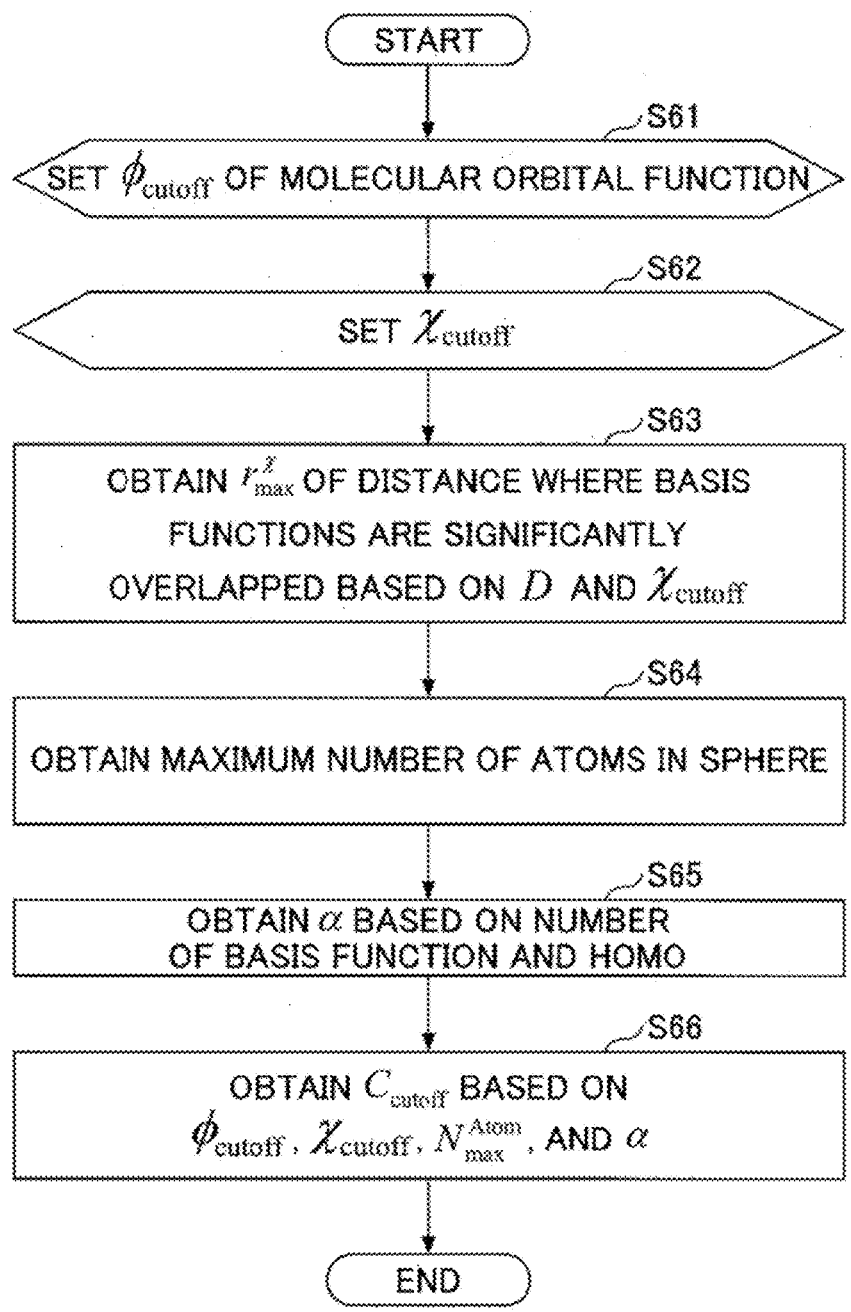
FIG. 6 is a flowchart for explaining a threshold determination process.

FIG. 6 is a flowchart for explaining a threshold determination process. In FIG. 6, the threshold determination part 45 sets the drawing threshold $\phi_{cutoff}$ of the molecular orbital functions (step S61). Also, the threshold determination part 45 calculates and sets the basis threshold $\chi_{cutoff}$ in which the influence to other basis functions becomes sufficiently small in the space distribution of the basis function (step S62).

The threshold determination part 45 acquires the threshold $r^\chi_{max}$ of the distance where the basis function and other basis functions are significantly overlapped based on a distribution function D and the basis threshold $\chi_{cutoff}$ of the basis function χ (step S63). The threshold determination part 45 acquires a maximum value of the number of atoms in the sphere of the radius $2r^\chi_{max}$ from each of the atoms, and sets the maximum number $N^{Atom}_{max}$ (step S64). Moreover, the threshold determination part 45 acquires α based on the number of the basis functions and the HOMO (step S65). Instead of the HOMO, α related to the LUMO may be acquired. The user may indicate the HOMO or LUMO beforehand.

Next, the threshold determination part 45 obtain the coefficient threshold $C_{cutoff}$ based on the drawing threshold $\phi_{cutoff}$, the basis threshold $\chi_{cutoff}$ and the maximum value $N^{Atom}_{max}$, and α (step S66).

Based on the coefficient threshold $C_{cutoff}$ determined in a process conducted by the threshold determination part 45, the data deletion storage part 46 creates and stores contents of the second MO data 136 in the storage part 130.

Figure 7:
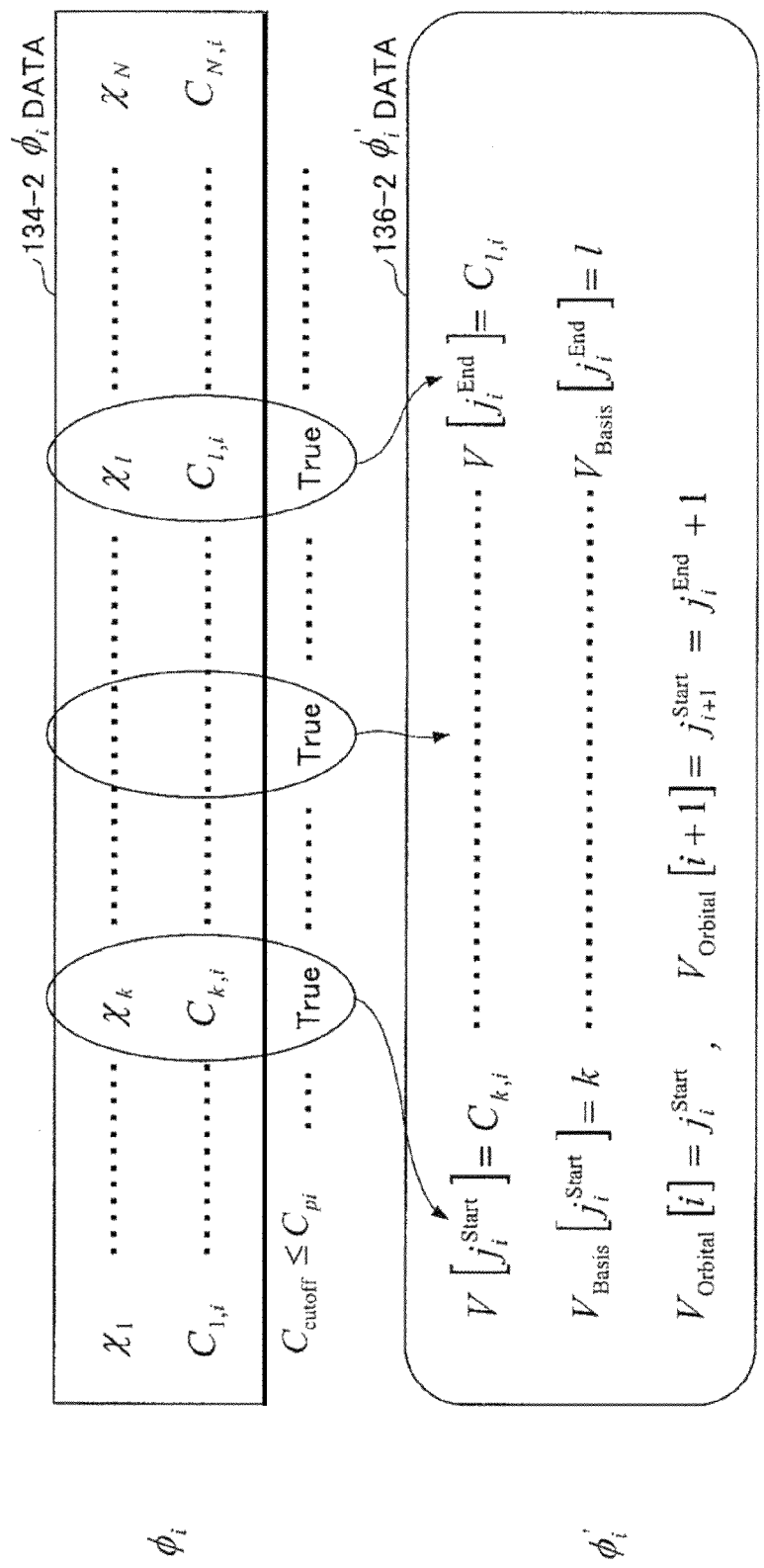
FIG. 7 is a diagram for explaining a data reduction process concerning an $i^{th}$ molecular orbital function $\phi$.

A data reduction process will be described with reference to FIG. 7. For the $i^{th}$ molecular orbital function $\phi_i$, the data reduction process is performed by the data deletion storage part 46. FIG. 7 is a diagram for explaining the data reduction process concerning the $i^{th}$ molecular orbital function $\phi_i$. In FIG. 7, the $i^{th}$ molecular orbital function $\phi_i$ will be described by using $\phi_i$ data 134-2 pertinent to the $i^{th}$ molecular orbital function $\phi_i$ in the first MO data 134 stored in the storage part 130.

In the $\phi_i$ data 134-2, the expansion coefficients $C_{pi}$ pertinent to the basis functions $\chi_p$ (p=1, 2, ..., N) corresponding to the basis functions $\chi_1$ through $\chi_N$, respectively.

The data deletion storage part 46 stores the expansion coefficients $C_{pi}$ being greater than or equal to the coefficient threshold $C_{cutoff}$ in one dimensional array V. In an order of p from 1 to N, the expansion coefficients $C_{pi}$ being greater than or equal to the coefficient threshold $C_{cutoff}$ are stored in elements from $j_i^{start}$ to $j_i^{End}$ of the array V. The $j_i^{Start}$ indicates a first expansion coefficient $C_{pi}$ after the data reduction process related to the $i^{th}$ molecular orbital $\phi_i$ (may be called "molecular orbital function $\phi_i$"). The $j_i^{End}$ indicates a last expansion coefficient $C_{pi}$ after the data reduction process related to the $i^{th}$ molecular orbital $\phi_i$.

Also, when storing the expansion coefficients $C_{pi}$ (greater than or equal to the coefficient threshold $C_{cutoff}$) after the data reduction, the data deletion storage part 46 stores pointers to the basis functions $\chi_p$ corresponding to the expansion coefficient $C_{pi}$ being greater than or equal to the coefficient threshold $C_{cutoff}$ to elements from $j_i^{start}$ to $j_i^{End}$ of the array $V_{Basis}$.

Furthermore, the data deletion storage part 46 manages elements from $j_i^{start}$ to $j^{End}$ by using one dimensional array $V_{Orbital}$. By setting $j_i^{Start}$ to an $i^{th}$ element ($V_{Orbital}[i]$) of the array $V_{Orbital}$ the element number is acquired by deducting $V_{Orbital}[i]$ from $V_{Orbital}[i+1]$.

As described above, $\phi_i'$ data 136-2 pertinent to the $i^{th}$ molecular orbital $\phi_i$ are created. In the $\phi_i'$ data 136-2, data from the array $V[j_i^{Start}]$ to the array $V[j_i^{End}]$ correspond to a part of the expansion coefficient data 6b in the second MO data 136 in FIG. 2. Data from the array $V_{Basis}[j_i^{Start}]$ to the array $V_{Basis}[j_i^{End}]$ correspond to a part of the basis function indication data 6c. The array $V_{orbital}[i]$ corresponds to a part of the MO indication data 6d.

In order to approximate the above expression (1), the expression (1) may be replaced by using an array based on the following relational expression (A).

$$C_{pi} => V[i],$$

$$\chi_p => \chi_{VBasis[l]},$$

$$N => j_i^{End} - j_i^{Start} + 1 = V_{Orbital}[i+1] - V_{Orbital}[i] \quad <\text{Relational Expression A}>$$

The expansion coefficient $C_{pi}$ is represented by V[1], and $\chi_p$ is represented by $\chi_{VBasis[1]}$. Also, the total number N of the basis functions is represented by the number ($j_i^{End} - j_i^{Start} + 1 = V_{Orbital}[i+1] - V_{Orbital}[i]$) of the basis functions to be applied.

As described above, by approximating the above expression (1), the expression (1) may be represented by an approximated molecular functions such as the following expression (7).

$$\phi_i \cong \phi_i' = \sum_{i=V_{Orbital}[i]}^{V_{Orbital}[i+1]-1} V[l] \chi_{V_{Basis}[i]} \quad (7)$$

Also, in a case of a related art in which the embodiment is not applied, the number of the basis functions $\chi_p$ pertaining to the $i^{th}$ molecular orbital $\phi_i$ becomes the total number N of the basis functions $\chi_p$. On the other hand, in a case of applying the embodiment, the number of the basis functions $\chi_p$ pertaining to the $i^{th}$ molecular orbital $\phi_i$ becomes the element number acquired by a calculation ($V_{Orbital}[i+1] - V_{Orbital}[i]$). Accordingly, a ratio of a calculation amount of the MO drawing part 48 in the embodiment with respect to that of the related art is indicated by the following expression (8).

$$\frac{V_{Orbital}[i+1] - V_{Orbital}[i]}{N} \quad (8)$$

The smaller the ratio acquired by the above expression (8) is, at the higher speed the drawing process is performed by the MO drawing part 48.

Figure 8A:
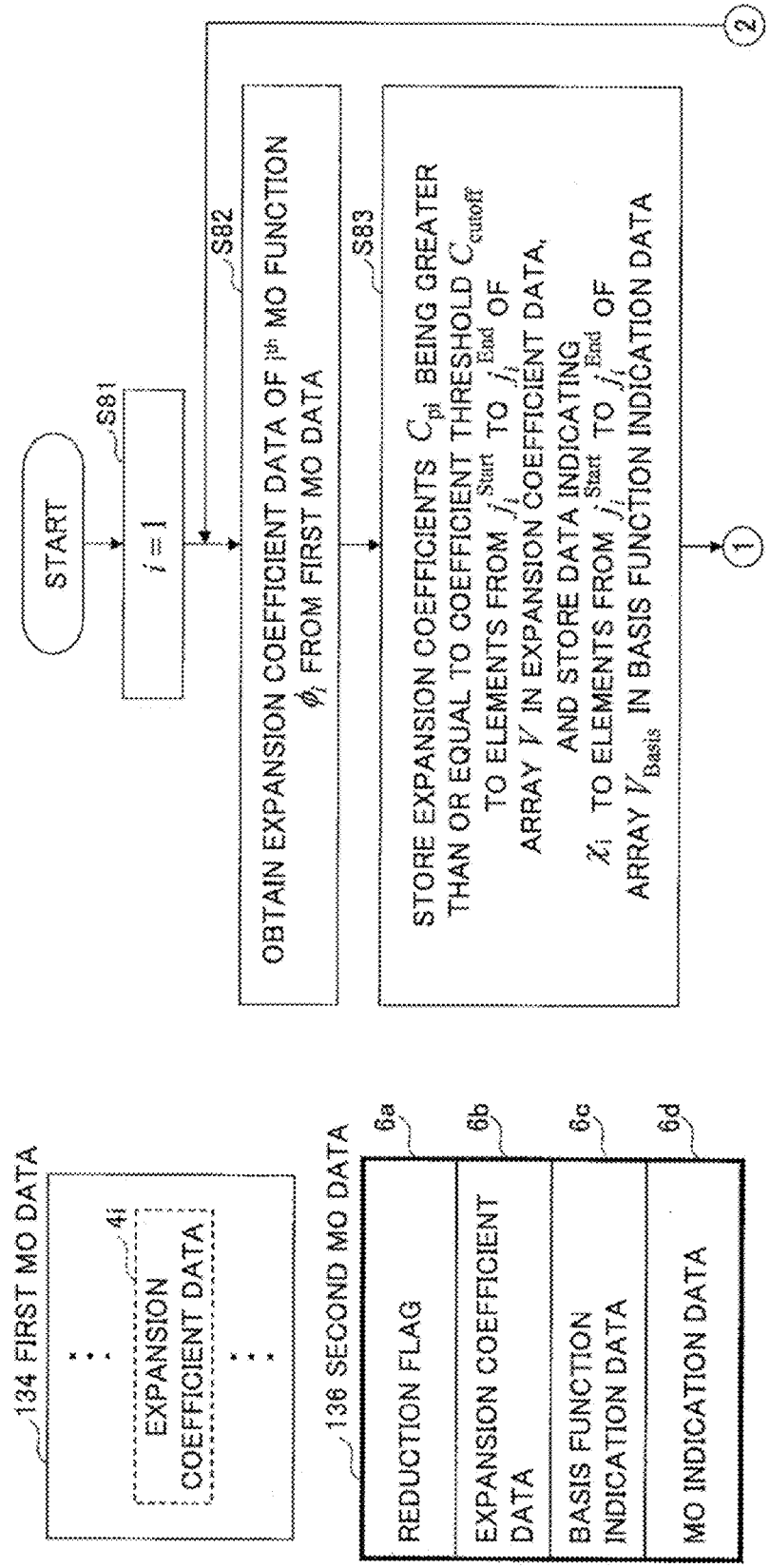
FIG. 8A and FIG. 8B are flowcharts for explaining a data deletion storing process performed by a data deletion storage part.
Figure 8B:
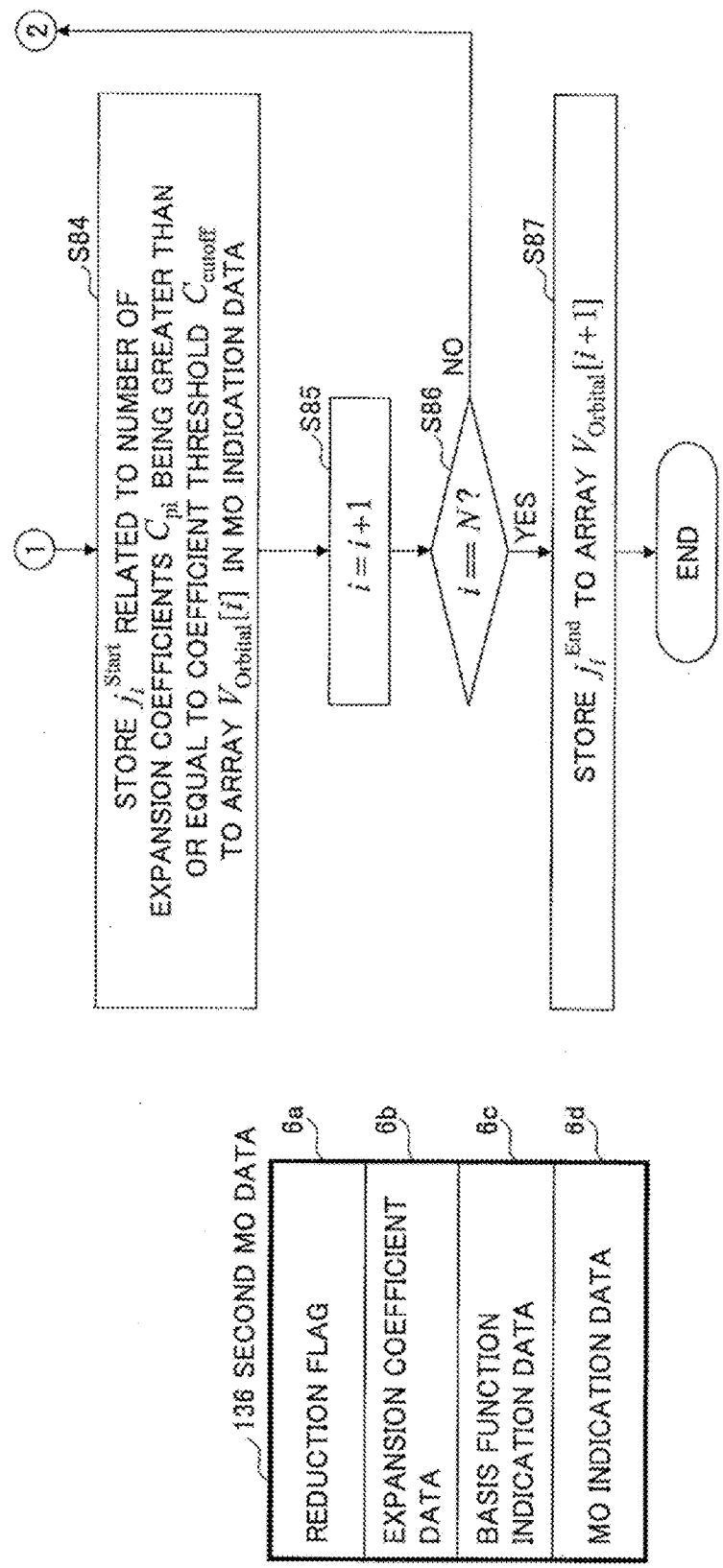

A data deletion storing process will be described with reference to FIG. 8A and FIG. 8B. The data deletion storing process is performed by the data deletion storage part 46 for all molecular orbital functions $\phi_i$. FIG. 8A and FIG. 8B are flowcharts for explaining a data deletion storing process performed by the data deletion storage part 46. In FIG. 8A, the data deletion storage part 46 sets 1 to a variable i (step S81). The data deletion storage part 46 acquires expansion coefficient data 4i of the $i^{th}$ molecular orbital $\phi_i$ from the first MO data 134 stored in the storage part 130 (step S82).

The data deletion storage part 46 stores the expansion coefficients $C_{pi}$ being greater than or equal to coefficient threshold $C_{cutoff}$ calculated by a threshold determination part 45 to the elements from $j_i^{Start}$ to $j_i^{End}$ of the array V in the expansion coefficient data 6b. Also, the data deletion storage part 46 stores data indicating the basis functions $\chi_i$ to the elements from $j_i^{Start}$ to $j_i^{End}$ of the array $V_{Basis}$ in the basis function indication data 6c (step S83).

Next, in FIG. 8B, the data deletion storage part 46 stores $j_i^{Start}$ to the array $V_{Orbital}[i]$ related to the number of the expansion coefficients $C_{pi}$ being greater than or equal to coefficient threshold $C_{cutoff}$ in the MO indication data 6d (step S84).

After that, the data deletion storage part 46 increments the variable i by 1 (step S85), and determines whether the variable i reaches the total number N of the molecular orbital functions $\phi$, that is, whether the variable i is equal to the total number N (step S86). If the variable i is not equal to the total number N, the data deletion storage part 46 goes back to the step S82, and repeats the above described processes. On the other hand, if the variable i is equal to the total number N of molecular orbital functions $\phi$, the data deletion storage part 46 stores a value where 1 is added to $j_i^{End}$ in the array $V_{Orbital}[i+1]$ (step S87). Then, the data deletion storing process is terminated.

Figure 9:
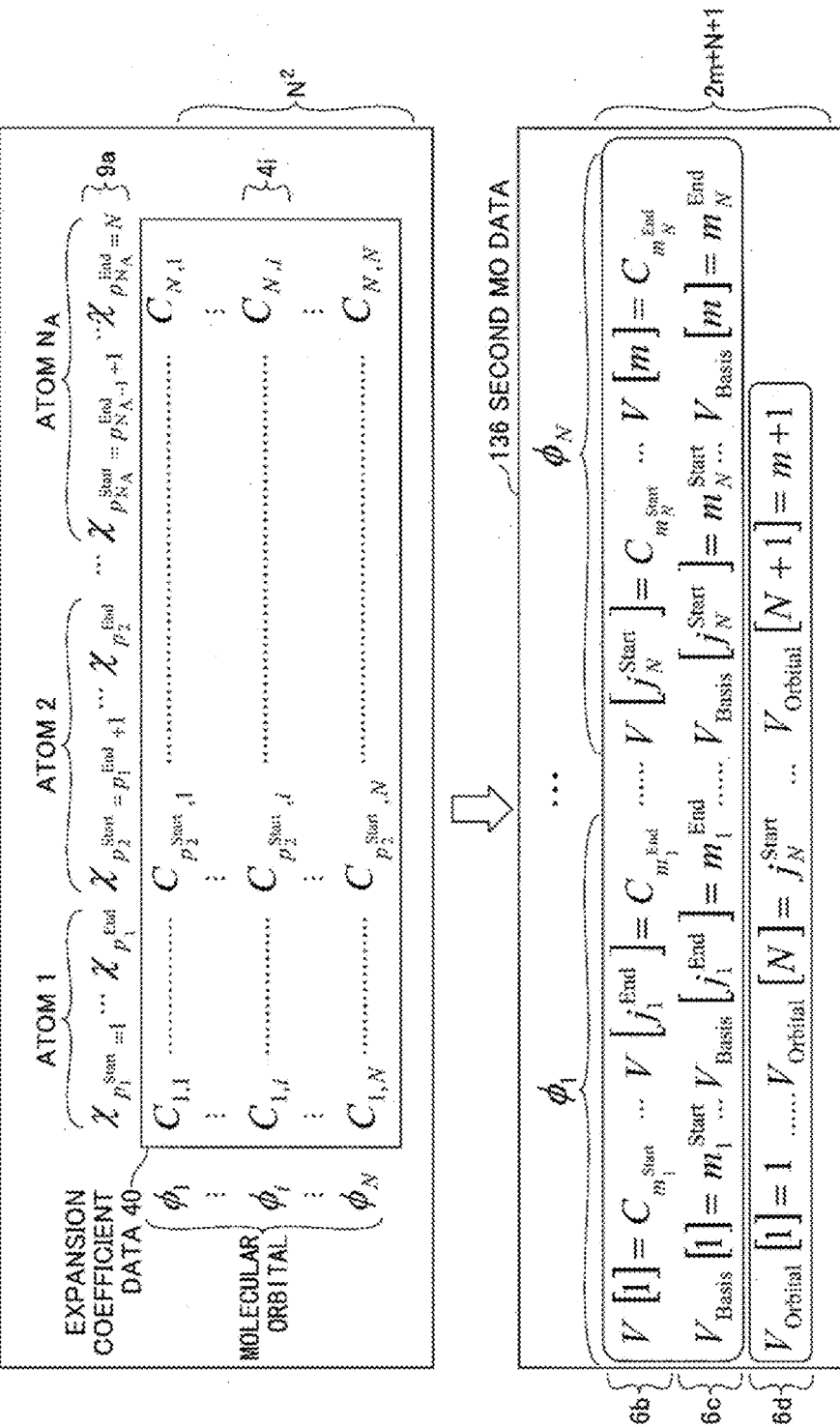
FIG. 9 is a diagram illustrating an example of second MO data.

The second MO data 136 will be described with reference to FIG. 9. The second MO data 136 are created by the MO data reduction part 47 including the threshold determination part 45 and the data deletion storage part 46. FIG. 9 is a diagram illustrating an example of the second MO data 136. FIG. 9 illustrates a case in which the second MO data 136 are created by the MO data reduction part 47 by deleting data from the first MO data 134 created by the MO function expansion part 44.

The first MO data 134 is created by the MO function expansion part 44. In the first MO data 134, the expansion coefficients C are stored by corresponding to the basis functions $\chi$, respectively, for each of the molecular orbitals $\phi$ based on the molecular structure design data 132.

For each of an atom 1, an atom 2, . . . , an atom $N_A$ included in the molecular structure, one or more basis functions $\chi$ are prepared beforehand. $N_A$ indicates the number of the atoms in a molecule. The total number (that is, the total number of the molecular orbitals $\phi$) of the basis functions $\chi$ pertinent to the atom 1 through the atom $N_A$ is indicated by N. The basis functions $\chi$ are independent functions. The total number of the expansion coefficients C is represented by N to the power of 2 ($N^2$). The expansion coefficient data 6b include N squared values of the expansion coefficients C.

The basis functions $\chi$ for depicting orbitals of the atom 1 are represented with suffixes $p_1^{Start}$ through $p_1^{End}$, respectively. The basis functions $\chi$ for depicting orbitals of the atom 2 are represented with suffixes $p_2^{Start}$ through $p_2^{End}$, respectively. The basis functions $\chi$ for depicting orbitals of the atom $N_A$ are represented with suffixes $p_{NA}^{Start}$ through $p_{NA}^{End}$, respectively. The $p_1^{Start}$ indicates a $1^{st}$ basis function $\chi$, and $p_{NA}^{End}$ indicates a $N^{th}$ basis function $\chi$.

Each of the molecular orbitals $\phi$ is specified by the suffix i (i=1, . . . , N), and the expansion coefficient data 4i indicates data of the molecule orbitals $\phi i$ in the expansion coefficient data 40. The expansion coefficient data 6b may be represented by a two dimensional array of N×N. For each of the expansion coefficients C, a first suffix indicates one of the basis functions $\chi$, and a second suffix indicates one of the molecular orbitals $\phi$. For the $1^{st}$ suffix, $p_i^{Start}$ is a number to indicate a first function in the basis functions related to the $i^{th}$ atom, and $p_i^{End}$ is a number to indicate a last function in the basis functions related to the $i^{th}$ atom.

The first MO data 134 may include basis function data 9a representing each of the basis functions $\chi$. Alternatively, the basis function data 9a may be separately stored in another data file, table, or the like.

In the second MO data 136 created by the MO data reduction part 47 based on the first MO data 134, the expansion coefficients C from the molecular orbital $\phi_1$ to the molecular orbital $\phi_N$ are stored to the array V in the expansion coefficient data 6b.

For the first molecular orbital $\phi_1$, the expansion coefficients C, which are greater than or equal to coefficient threshold $C_{cutoff}$, are stored to the elements from the $1^{st}$ to $J_1^{End}$ in the array V. A first expression coefficient C is represented with a suffix $m_1^{Start}$ and a last expression coefficient C is represented with a suffix $m_1^{End}$. For the last molecular orbital $\phi_N$, the expansion coefficients C, which are greater than or equal to coefficient threshold $C_{cutoff}$, are stored to the elements from the $J_N^{Start}$ to m in the array V. The first expansion coefficient C is represented with a suffix $m_N^{Start}$, and the last expansion coefficient C is represented with a suffix $m_N^{End}$.

In the basis function indication data 6c, the basis functions $\chi$, which are used to depict the molecular orbitals $\phi_1$ through $\phi_N$, are stored in the array $V_{Basis}$ according to an array order of the expansion coefficients C stored in the expansion coefficient 6b.

For the first molecular orbital $\phi_1$, the basis function $\chi$, where the first expansion coefficient C with the suffix $m_1^{Start}$ of the array V is used, is stored to the first element of the array $V_{Basis}$. Also, the basis function $\chi$, where the last expansion coefficient C with the suffix $m_1^{End}$ of the array V is used, is stored to the $J_1^{End}$ element of the array $V_{Basis}$. Other molecular orbitals $\phi_i$ will be explained in the same manner.

In the MO indication data 6d, the number identifying the element where the first expansion coefficient C is indicated by the array $V_{Orbital}$ for each of the molecular orbitals $\phi_1$ to $\phi_N$. A first element number $j_i^{Start}$ of the $i^{th}$ molecular orbital $\phi$ in the array V is stored in $V_{orbital}[i]$. A value resulted from adding 1 to the number m of the expansion coefficients C after the data are reduced is stored to a last element $V_{Orbital}$ [N+1] of the array $V_{Orbital}$. In the embodiment, when the MO data reduction part 47 is applied so that the second MO data 136 is valid, the number m may be also the number of the basis functions $\chi$ which are deleted. Accordingly, in a molecular orbital drawing process conducted by the MO drawing part 48, it is possible to reduce the drawing process by the number m of the basis functions $\chi$ which are deleted.

In order to acquire molecular orbital function values of a drawing target from the expansion coefficient data 6b of the molecular orbitals, it is determined whether data for the drawing process are stored in a regular data format (corresponding to the first MO data 134 including the entire data) in which the embodiment is applied or in a reduced data format (corresponding to the second MO data 136) in which the embodiment is applied and the data amount is reduced. The reduction flag 6a may be used If it is determined, by checking whether the reduction flag 6a indicates "True" or "False", that the data in the regular data format are to be used for the drawing process, the molecular orbit function values are calculated by the expression (1) using the first MO data 134 in the regular data format, and the drawing process is performed.

If it is determined that the second MO data 136 in the reduced data format are to be used for the drawing process, since the regular data format of the first MO data 134 and the reduced data format of the second MO data 136 are corresponded to as illustrated in FIG. 7, values of approximate molecular orbital functions $\phi_i'$ are calculated by the above expression (7) based on the above described <Relational Expression A>. The molecular orbitals are drawn by using the values. In this case, compared with the regular data format, a drawing calculation amount is reduced at the ratio expressed by the expression (8).

Figure 10:
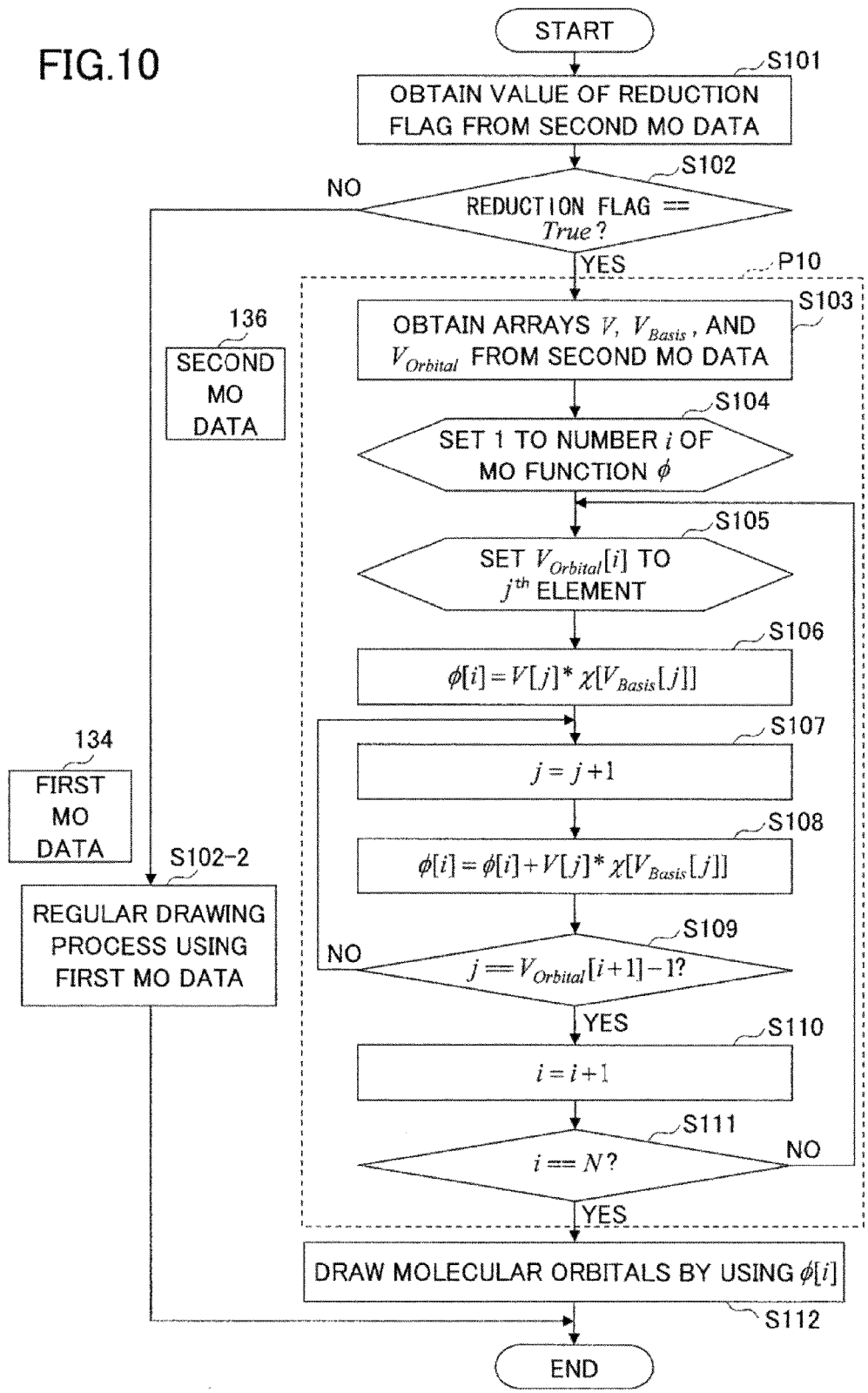
FIG. 10 is a flowchart for explaining a molecular orbital function determination process.

Next, a molecular orbital function determination process will be described with reference to FIG. 10. The molecular orbital function determination process is performed by the MO function determination part 49 of the MO drawing part 48 using the second MO data 136 to determine the molecular orbital functions. FIG. 10 is a flowchart for explaining the molecular orbital function determination process. In FIG. 10, steps S103 through S111 correspond to the molecular orbital function determination process P10 conducted by the MO function determination part 49.

The MO drawing part 48 acquires a value of the reduction flag 6a from the second MO data 136 stored in the storage part 130 (step S101).

The MO drawing part 48 determines whether the reduction flag 6a indicates "True", that is, whether the second MO data 136 is valid (step S102). When the reduction flag 6a indicates "False", that is, the second MO data 136 is invalid, the MO drawing part 48 performs a regular drawing process by the expression (1) using the first MO data 134 (step S102-2), and terminates the molecular orbital function determination process when the regular drawing process ends.

On the other hand, when the reduction flag 6a indicates "True", that is, the second MO data 136 is valid, the MO drawing part 48 instructs the MO function determination part 49 to perform the molecular orbital function determination process. The MO function determination part 49 reads out the expansion coefficient data 6b, the basis function indication data 6c, and the MO indication data 6d from the second MO data 136, and acquires the array V, the array $V_{Basis}$, and the array $V_{Orbital}$ (step S103).

The MO function determination part 49 sets 1 to a number variable i specifying the $i^{th}$ molecular orbital function $\phi$ (step S104), and sets $V_{orbital}[i]$ to an element number variable j (step S105). The element number variable j specifies the both element numbers in the array V for storing the expansion coefficients C and the array $V_{Basis}$ of the basis function $\chi$, which are applied for the molecular orbital function $\phi_i$. In a process in the step S105, the first element number of the molecular orbital function $\phi_i$ is set to the element number variable j.

The MO function determination part 49 sets an expression for multiplying the expansion coefficient C with the basis function $\chi$ respective to the first element number, to the element i of an array $\phi$ representing the molecular orbital function $\phi_i$ ($\phi[i]$) (step S106).

$$\phi[i]=V[j]*\chi[V_{Basis}[j]] \qquad (9)$$

The MO function determination part 49 increments the element number variable j (step S107), and additionally sets an expression for multiplying the expansion coefficient C and the basis function $\chi$ respective to the element number variable j, to the element I ($\phi[i]$) (step S108).

$$\phi[i]=\phi[i]+V[j]*\chi[V_{Basis}[j]] \qquad (10)$$

Accordingly, the MO function determination part 49 determines whether the element number variable j is equal to the last element number in the molecular orbital function $\phi_i$ (step S109). The MO function determination part 49 acquires the array $V_{Orbital}[i+1]$, and deducts 1 from the array $V_{Orbital}[i+1]$. Thus, the element number indicating the last element is acquired. The MO function determination part 49 may determine whether the element number variable j reaches a value resulted from deducting 1 from the array $V_{Orbital}[i+1]$. When the element number variable j has not reached the last element number in the molecular orbital function $\phi_i$, that is, when the element number variable j is not equal to the last element number, the MO function determination part 49 returns to step S107.

On the other hand, in step S109, when the element number variable j is equal to the last element number in the molecular orbital function $\phi_i$, the MO function determination part 49 increments the number variable i of the molecular orbital function $\phi$ by 1 (step S110), and determines whether the number variable i reaches the total number N of the molecular orbital function $\phi$ by checking whether the number variable i is equal to the total number N (step S111). The MO function determination part 49 may determine whether the number variable i is equal to the total number N. When the number variable i is not equal to the total number N, the MO function determination part 49 goes back to step S105 and repeats the above described process.

On the other hand, when the number variable i is equal to the total number N, the MO drawing part 48 determines that all molecular orbital functions $\phi_i$ are defined by the MO function determination part 49, and draws the molecular orbitals at the display device 15 by using the defined molecular orbital functions $\phi_i$ (step S112). After the molecular orbitals are drawn, the MO drawing part 48 terminates the molecular orbital function determination process.

Next, a comparison result of data amounts will be described. The data amount in a case of applying the data reduction according to the embodiment is compared with the data amount in a case in which the embodiment is not applied.

Figure 11:
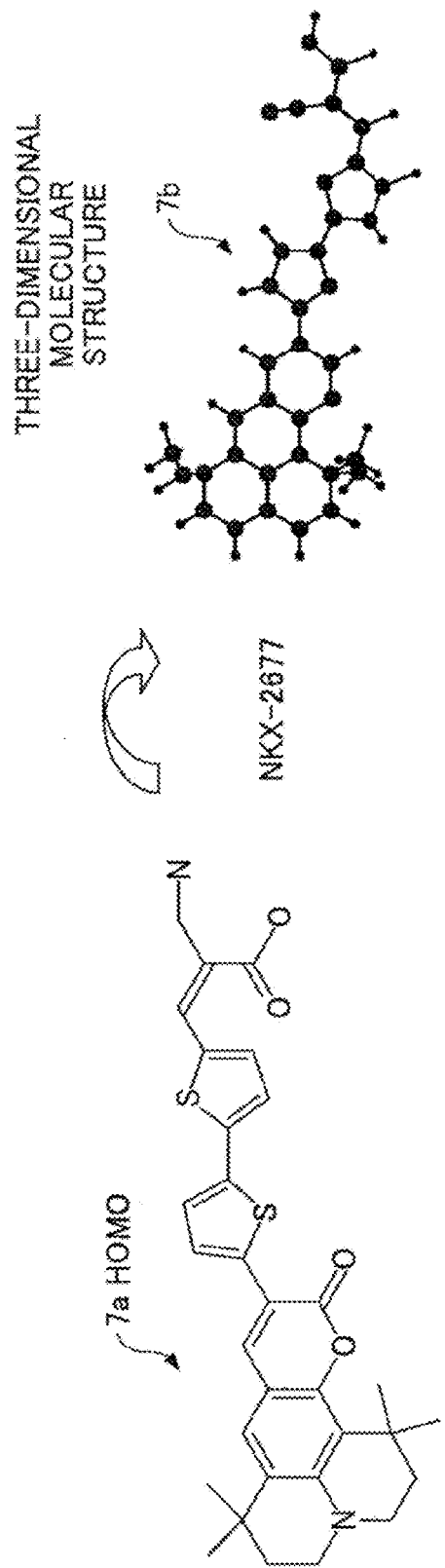
FIG. 11 is a diagram for explaining a comparison of data amounts in a first drawing example.
Figure 12:
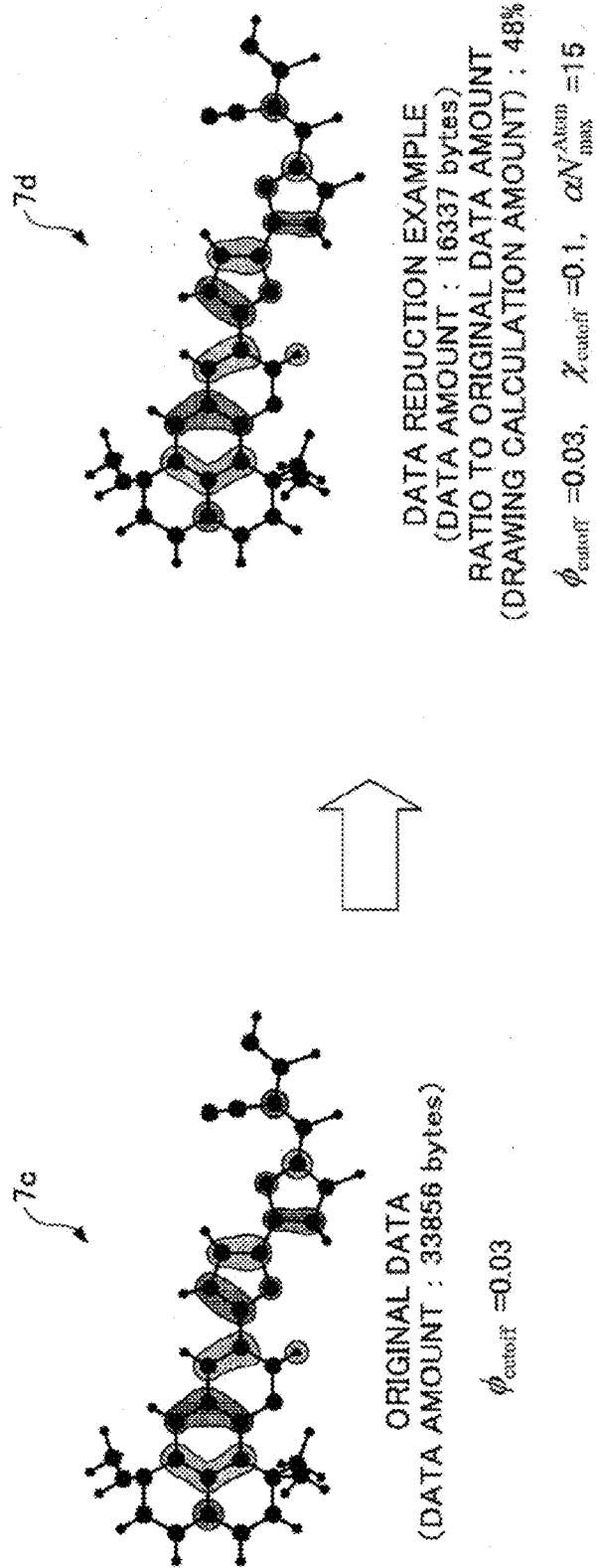
FIG. 12 is a diagram for explaining the comparison of data amounts in the first drawing example.

A first drawing example in a case of drawing the HOMO of an organic molecule NKX-2677 will be described with FIG. 11 and FIG. 12. The first drawing example will be depicted in a case of using an Austin Model 1 (AM1) method. FIG. 11 and FIG. 12 are diagrams for explaining a comparison of the data amounts in the first drawing example.

FIG. 11 illustrates a state in which a three-dimensional molecular structure 7b of NKX-2677 from molecular structure data of a HOMO 7a of NKX-2677. Then, the comparison of the data amounts in a case of performing a molecular orbital calculation by using the AM1 will be illustrated in FIG. 12.

In FIG. 12, a three-dimensional molecular structure 7c is illustrated in which the molecular orbitals are drawn in a case in which the data reduction according to the embodiment is not applied. For the three-dimensional molecular structure 7c, original data, that is, the data amount of "33856" bytes are used to calculate the molecular orbitals by the MO function expansion part 44. As illustrated in FIG. 9, in a case of performing the AM1 method, the data amount concerning the expansion coefficients C of the molecular orbitals $\phi$ corresponds to that of the expansion coefficient data 40 (FIG. 9). That is, the data amount is regarded as $N^2$ values of the expansion coefficients C.

On the other hand, when the data reduction according to the embodiment is conducted, the second MO data 136, which is reduced by the MO data reduction part 47, are used in a three-dimensional molecular structure 7d in which the molecular orbitals are drawn. In this case, the data amount of "16337" bytes, which are reduced from the original data (for example, the first MO data 134), are used. A ratio to the original data amount (drawing calculation amount) indicates 48%. As illustrated in FIG. 9, the number m of the expansion coefficients C after the data reduction performed to the expansion coefficient data 6b corresponds to the reduced data amount.

As described above, by including a functional configuration according to the embodiment as illustrated in FIG. 2 and the like, in the first drawing example, it is possible to reduce the data amount by approximately one-half. Also, in the three-dimensional molecular structure 7d, the approximate molecular orbital functions are depicted with the same quality as the three-dimensional molecular structure 7c. As described above, it is possible to acquire a pertinent drawing result of the molecular orbitals while reducing the calculation amount by the functional configuration according to the embodiment.

Figure 13:
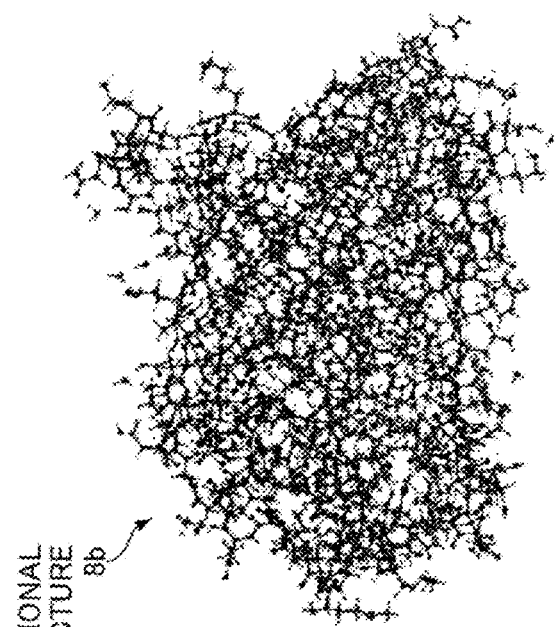
FIG. 13 is a diagram for explaining a comparison of the data amounts in a second drawing example.
Figure 13:
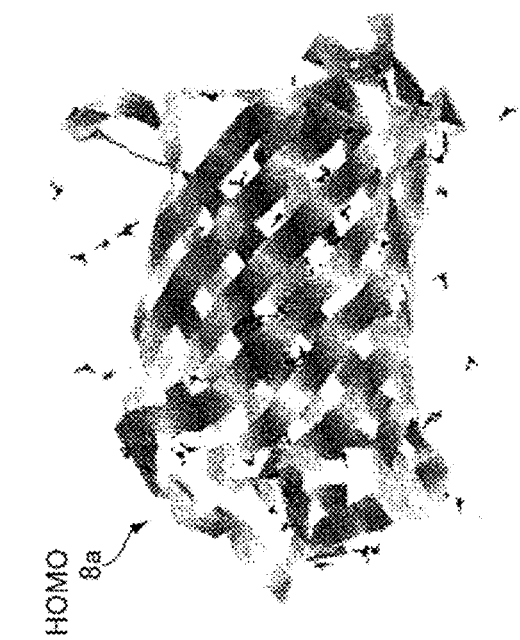
Figure 14:
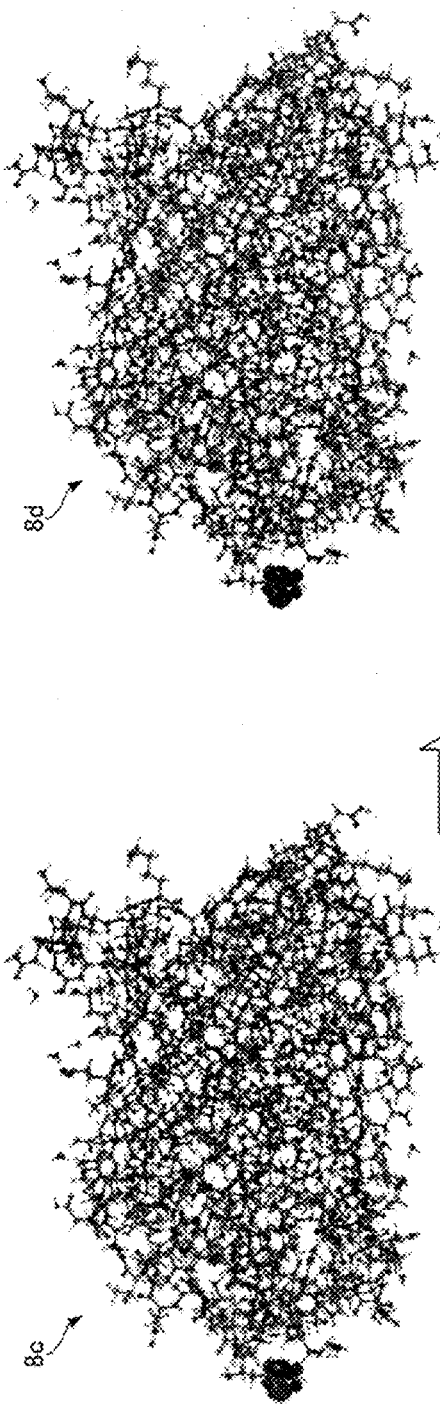
FIG. 14 is a diagram for explaining the comparison of the data amount in the second drawing example.

A second drawing example will be described with reference to FIG. 13 and FIG. 14. In the second drawing example, the HOMO of a protein molecular 1BFP ($C_{1156}H_{1941}N_{310}O_{428}S_7$) is depicted. In the second drawing example, a case of using the AM1 method is illustrated. FIG. 13 and FIG. 14 are diagrams for explaining a comparison of the data amounts in the second drawing example.

In FIG. 13, a three-dimensional structure 8b is created and depicted by representing a ball and stick model based on molecular structure data of a HOMO 8a of the protein molecular 1BFP represented by a ribbon model, in a state in which hydrogen of the protein molecular 1BFP is added. In a case of performing the molecular orbital calculation using the AM1, a comparison of data mounts is illustrated in FIG. 14.

In FIG. 14, the three-dimensional molecular structure 8c is illustrated in a case in which the data reduction according to the embodiment is not applied and the molecular orbitals are drawn. In this case, the original data, that is, the data amount of "91107025" bytes calculated by the MO function expansion part 44 are used. As illustrated in FIG. 9, the data amount pertinent to the expansion coefficients C of the molecular orbitals $\phi$, which are stored in the case of performing the AM1 method, correspond to that of the expansion coefficient data 40. The data amount is regarded as $N^2$ values of the expansion coefficients C.

In a three-dimensional molecular structure 8d is illustrated in a case in which the data reduction according to the embodiment is applied and the molecular orbitals are drawn. In this case, the second MO data 136 reduced by the MO data reduction part 47 are used. That is, the data amount of "3232281" bytes, which is reduced from the original data (which may be the first MO data 134), is used. A ratio to the original data amount (drawing calculation amount) indicates 3.5%. As illustrated in FIG. 9, the number m of the expansion coefficients C after the data reduction performed to the expansion coefficient data 6b corresponds to the reduced data amount.

As described above, by including the functional configuration according to the embodiment as illustrated in FIG. 2 and the like, it is also possible to significantly reduce the data amount in the second drawing example. Also, in the three-dimensional molecular structure 8d, the approximate molecular orbital functions are depicted with the same quality as the three-dimensional molecular structure 8c. As described above, it is possible to acquire a pertinent drawing result of the molecular orbitals while reducing the calculation amount by the functional configuration according to the embodiment.

Compared to the related art, even if lattice points are reduced, the data amount of the expansion coefficients C acquired in the molecular orbital calculation is not reduced. Regarding the total number N of independent basis functions, the data amount of the expansion coefficients of the molecular orbitals exponentially increases by N squared ($N^2$). In a case of storing the expansion coefficients C, which are related to multiple large scale molecules, to reuse the expansion coefficients C, the storage part 130 of the molecular design apparatus may be considerably consumed.

On the other hand, in the molecular design apparatus according to the embodiment, the molecular orbital functions $\phi$ are used in which the molecular orbital functions $\phi$ are reduced by using the coefficient threshold $C_{cutoff}$ of the expansion coefficients C based on the drawing threshold $\phi_{cutoff}$ indicating a constant function value to draw the molecular orbital functions $\phi$ as the isosurface of the constant function value. The molecular orbital functions $\phi$ are represented by the basis functions $\chi$ and the expansion coefficients C. Thus, it is possible to conduct the drawing process of the molecular orbitals and to visually draw the molecular orbitals at higher speed so that the molecular orbitals are intuitively comprehensible.

Accordingly, it is possible to provide the molecular design apparatus in which the data amount is significantly reduced while retaining drawing information of the molecular orbitals, instead of losing the drawing information. It is possible to draw the molecular orbitals at higher speed, and to considerably reduce a storage area for the data amount.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A molecular design apparatus, comprising:
    a storage part configured to store molecular structure design data;
    a molecular orbital function expansion part configured to calculate expansion coefficients applied to basis functions by expanding a molecular orbital function used to draw molecular orbitals based on the molecular structure design data, and stores to the storage part first molecular orbital data, the expansion coefficients corresponding to the basis functions;
    a molecular orbital data reduction part configured to determine a coefficient threshold for the expansion coefficients of the basis functions acquired by the molecular orbital function expansion part by using a drawing threshold which indicates a constant function value to draw the molecular orbital functions as an isosurface of the constant function value on a screen of a display device, and to store to the storage part second molecular orbital data in which the expansion coefficients of the basis functions are reduced based on the coefficient threshold; and
    a molecular orbital drawing part configured to draw the molecular orbitals on the screen of the display device by using the second molecular orbital data stored in the storage part,
    wherein the molecular orbital data reduction part includes a threshold determination part configured to set a basis threshold indicating function values in a range for ignoring overlaps of a basis function to other basis functions for each of the basis functions in the molecular orbital function, to calculate a coordinate threshold indicating a coordinate value corresponding to the basis threshold, to calculate a maximum value of a number of atoms included in a sphere having a predetermined radius based on the coordinate threshold from a center coordinate of each of the atoms forming a molecule, to calculate a value where a ratio of a total electron number of the molecule to a total number of the basis functions is multiplied to a number of the basis functions for each of the atoms or a basis ratio corresponding to the value, and to determine the coefficient threshold based on the drawing threshold, the basis threshold, the maximum value of the number of the atoms, and the basis ratio.

2. The molecular design apparatus as claimed in claim 1, wherein the molecular orbital data reduction part includes a data deletion storage part configured to store the second molecular orbital data including the expansion coefficients being greater than or equal to the coefficient threshold determined by the threshold determination part by referring to the first molecular orbital data.

3. The molecular design apparatus as claimed in claim 2, wherein the second molecular orbital data includes
    a coefficient array which stores the expansion coefficients being greater than or equal to the coefficient threshold;
    a basis function indication array in which an element number thereof is equal to the element number of the coefficient array and stores pointers to the basis functions; and
    a molecular orbital indication array in which the element number thereof is equal to a total number of the basis functions or is one more than the element number of the basis functions, and which stores a pointer to a first expansion coefficient for each of the molecular orbital functions in the expansion coefficient data, and
    when the molecular orbital data reduction part stores the second molecular orbital data in the storage part, a reduction flag in the storage part is set to indicate that the expansion coefficients are reduced in which the reduction flag is not set when the first molecular orbital data is stored in the storage part.

4. The molecular design apparatus as claimed in claim 3, wherein the molecular orbital drawing part includes:
    a molecular orbital function determination part configured to determine each of approximate orbital functions approximating the molecular orbital functions by using the coefficient array, the basis function indication array, and the molecular orbital indication array in the second molecular orbital data, when the reduction flag indicates that the expansion coefficients are reduced.

5. The molecular design apparatus as claimed in claim 4, wherein the molecular orbital drawing part draws the molecular orbitals by using the first molecular orbital data when the reduction flag does not indicate that the expansion coefficients are reduced.

6. A molecular design method performed in a computer, the method comprising:
    calculating, by the computer, expansion coefficients pertinent to basis functions by expanding molecular orbital functions used to draw molecular orbitals to the basis functions based on molecular structure design data stored in a storage part, and stores first molecular orbital data, the expansion coefficients corresponding to the basis functions, to the storage part;
    determining, by the computer, a coefficient threshold with respect to the expansion coefficients of the basis functions acquired in the calculating, by using a drawing threshold which indicates a constant function value to draw the molecular orbital functions as an isosurface of the constant function value on a screen of a display device;

storing, by the computer, second molecular orbital data in which the expansion coefficients of the basis functions are reduced based on the coefficient threshold to the storage part; and drawing, by the computer, the molecular orbitals on the screen of the display device by using the second molecular orbital data stored in the storage part wherein the determining of the coefficient threshold includes setting a basis threshold indicating function values in a range for ignoring overlaps of a basis function to other basis functions for each of the basis functions in the molecular orbital function, calculating a coordinate threshold indicating a coordinate value corresponding to the basis threshold, calculating a maximum value of a number of atoms included in a sphere having a predetermined radius based on the coordinate threshold from a center coordinate of each of the atoms forming a molecule, calculating a value where a ratio of a total electron number of the molecule to a total number of the basis functions is multiplied to a number of the basis functions for each of the atoms or a basis ratio corresponding to the value, and determining the coefficient threshold based on the drawing threshold, the basis threshold, the maximum value of the number of the atoms, and the basis ratio.

7. A non-transitory computer-readable recording medium having stored therein a program for causing a computer to execute a molecular design process comprising:

calculating expansion coefficients pertinent to basis functions by expanding molecular orbital functions used to draw molecular orbitals to the basis functions based on molecular structure design data stored in a storage part, and stores first molecular orbital data, the expansion coefficients corresponding to the basis functions, to the storage part;

determining a coefficient threshold with respect to the expansion coefficients of the basis functions acquired in the calculating, by using a drawing threshold which indicates a constant function value to draw the molecular orbital functions as an isosurface of the constant function value on a screen of a display device;

storing second molecular orbital data in which the expansion coefficients of the basis functions are reduced based on the coefficient threshold to the storage part; and drawing the molecular orbitals on the screen of the display device by using the second molecular orbital data stored in the storage part wherein the determining of the coefficient threshold includes setting a basis threshold indicating function values in a range for ignoring overlaps of a basis function to other basis functions for each of the basis functions in the molecular orbital function, calculating a coordinate threshold indicating a coordinate value corresponding to the basis threshold, calculating a maximum value of a number of atoms included in a sphere having a predetermined radius based on the coordinate threshold from a center coordinate of each of the atoms forming a molecule, calculating a value where a ratio of a total electron number of the molecule to a total number of the basis functions is multiplied to a number of the basis functions for each of the atoms or a basis ratio corresponding to the value, and determining the coefficient threshold based on the drawing threshold, the basis threshold, the maximum value of the number of the atoms, and the basis ratio.

* * * * *